United States Patent [19]

D'Alonzo et al.

[11] Patent Number: 5,679,706

[45] Date of Patent: Oct. 21, 1997

[54] COMBINATION OF A POTASSIUM CHANNEL ACTIVATOR AND AN ANTIARRHYTHMIC AGENT

[75] Inventors: Albert J. D'Alonzo, Hampton; Gary J. Grover, Stockton, both of N.J.

[73] Assignee: Bristol-Myers Squibb Company, Princeton, N.J.

[21] Appl. No.: 316,153

[22] Filed: Sep. 30, 1994

[51] Int. Cl.$^6$ ............ A61K 31/66; A61K 31/535; A61K 31/495; A61K 31/44; A61K 31/445; A61K 31/415; A61K 31/35

[52] U.S. Cl. ............ 514/456; 514/114; 514/235.5; 514/255; 514/278; 514/302; 514/318; 514/337; 514/392; 514/821

[58] Field of Search ............ 514/114, 235.5, 514/255, 278, 308, 337, 392, 456, 821

[56] References Cited

U.S. PATENT DOCUMENTS

| | | | |
|---|---|---|---|
| 4,721,809 | 1/1988 | Buzby et al. | 564/82 |
| 4,876,262 | 10/1989 | Oinuma et al. | 514/318 |
| 4,959,366 | 9/1990 | Cross et al. | 514/239 |
| 4,996,215 | 2/1991 | Oinuma et al. | 514/316 |
| 5,034,411 | 7/1991 | Almgren et al. | 514/522 |
| 5,089,526 | 2/1992 | Simon et al. | 514/605 |
| 5,140,031 | 8/1992 | Atwal et al. | 514/302 |
| 5,276,168 | 1/1994 | Atwal | 549/404 |
| 5,374,643 | 12/1994 | Atwal et al. | 514/364 |

FOREIGN PATENT DOCUMENTS

| | | |
|---|---|---|
| 0 431 943 | 6/1991 | European Pat. Off. . |
| 0 431 944 | 6/1991 | European Pat. Off. . |
| 0 431 945 | 6/1991 | European Pat. Off. . |

OTHER PUBLICATIONS

Yao et al., "Effects of the $K_{ATP}$ Channel Opener Bimakalim on Coronary Blood Flow, Monophasic Action Potential Duration, and Infarct Size in Dogs", *Cir.*, vol. 89, No. 4, 1994, pp. 1769–1775.

*Primary Examiner*—Kimberly Jordan
*Attorney, Agent, or Firm*—Ellen K. Park

[57] ABSTRACT

A method for the concomitant treatment of ischemia and arrhythmia in mammalian species which includes administering a combination of a potassium channel opener having little or no effect on action potential duration in the heart and a class III antiarrhythmic compound.

15 Claims, 4 Drawing Sheets

COMBINATION OF A POTASSIUM CHANNEL ACTIVATOR AND AN ANTIARRHYTHMIC AGENT

BRIEF DESCRIPTION OF THE INVENTION

The present invention is directed to a combination of a potassium channel activator having little or no effect on action potential duration (APD) in the heart and a class III antiarrhythmic agent for the concomitant treatment of myocardial ischemia and arrhythmia.

BRIEF DESCRIPTION OF THE FIGURES

As used in the figures and as referred to herein, compound A has the structure:

and the name: (3S-trans)-N-(chloro-phenyl)-N"-cyano-N'(6-cyano-3,4-dihydro-3-hydroxy-2,2-dimethyl-2H-1-benzopyran-4-yl)guanidine or BMS180,448.

FIG. 1 shows that the effects of cromakalim and compound A on time to contracture were nearly identical.

DETAILED DESCRIPTION OF THE INVENTION

Listed below are definitions of various terms used to describe the instant invention. These definitions apply to the terms as they are used throughout the specification (unless they are otherwise limited in specific instances) either individually or as part of a larger group.

The term "alkyl" refers to straight or branched chain saturated hydrocarbon radicals having up to 8 carbons, preferably from 1 to 5 carbons. Similarly, the terms "alkoxy" and "alkylthio" refer to such alkyl groups attached to an oxygen or sulfur atom respectively.

The term "alkenyl" refers to straight or branched chain hydrocarbon radicals having from 2 to 8 carbons and at least one double bond, preferably 3 to 5 carbons.

The term "alkynyl" refers to straight or branched chain hydrocarbon radicals having from 2 to 8 carbons and at least one triple bond, preferably 3 to 5 carbons.

The term "cycloalkyl" refers to saturated carbocyclic rings of 3 to 7 carbon atoms with cyclopropyl, cyclopentyl and cyclohexy being most preferred.

The term "halogen" or "halo" refers to chlorine, bromine, iodine or fluorine.

The term "halo substituted alkyl" or "haloalkyl" refers to such alkyl groups described above in which one or more hydrogens have been replaced by a halogen, such as trifluoromethyl, pentafluoroethyl, 2,2,2-trichloroethyl, chloromethyl, bromomethyl, etc., trifluoromethyl being preferred.

The term "aryl" refers to phenyl, 1-naphthyl, 2-naphthyl or mono substituted phenyl, 1-naphthyl, 2-naphthyl wherein said substituent is alkyl of 1 to 4 carbons, alkylthio of 1 to 4 carbons, alkoxy of 1 to 4 carbons, halo, nitro, cyano, hydroxy, amino, —NH-alkyl (wherein alkyl is of 1 to 4 carbons), —N(alkyl)$_2$ (wherein alkyl is of 1 to 4 carbons), —N($R_a$)COR$_a$', —N($R_a$)CO-haloalkyl, —N($R_a$)CO-amino, —N($R_a$)CO-substituted amino, —COR$_a$, —COOR$_a$ (wherein $R_a$ and $R_a$' are independently hydrogen, alkyl, haloalkyl, aryl or arylalkyl), —CF$_3$, —OCHF$_2$, (wherein $R_1$ is hydrogen, alkyl of 1 to 4 carbons, alkoxy of 1 to 4 carbons, alkylthio of 1 to 4 carbons, halo, hydroxy or —CF$_3$), —O—CH$_2$-cycloalkyl, or —S—CH$_2$-cycloalkyl, and di-substituted phenyl, 1-naphthyl or 2-naphthyl wherein said substituents are methyl, methoxy, methylthio, halo, —CF$_3$, nitro, amino, and —OCHF$_2$.

Preferred aryl groups include unsubstituted phenyl and monosubstituted phenyl wherein the substituent is nitro, halo, —CF$_3$, alkyl, cyano or methoxy.

The term "heterocyclo" refers to fully saturated or unsaturated rings of 5 or 6 atoms containing 1 or 2 oxygen and/or sulfur atoms and/or 1 to 4 nitrogen atoms provided that the total number of hetero atoms in the ring is 4 or less. The hetero ring is attached by way of an available carbon atom. Preferred monocyclic hetero groups include 2- and 3-thienyl, 2- and 3-furyl, 2-, 3- and 4-pyridyl, and imidazolyl. The term hetero also includes bicyclic rings wherein the 5 or 6 membered ring containing oxygen, sulfur and nitrogen atoms as defined above is fused to a benzene ring and the bicyclic ring is attached by way of an available carbon atom. Preferred bicyclic hetero groups include 4, 5, 6 or 7-indolyl, 4, 5, 6 or 7-isoindolyl, 5, 6, 7 or 8-quinolinyl, 5, 6, 7 or 8-isoquinolinyl, 4, 5, 6 or 7-benzothiazolyl, 4, 5, 6 or 7-benzoxazolyl, 4, 5, 6 or 7-benzimidazolyl, 4, 5, 6 or 7-benzoxadiazolyl, and 4, 5, 6 or 7-benzofuranzanyl.

The term "heterocyclo" also includes such monocyclic and bicyclic rings wherein an available carbon atom is substituted with an alkyl of 1 to 4 carbons, alkylthio of 1 to 4 carbons, alkoxy of 1 to 4 carbons, halo, nitro, keto, cyano, hydroxy, amino, —NH-alkyl (wherein alkyl is of 1 to 4 carbons), —N(alkyl)$_2$ (wherein alkyl is of 1 to 4 carbons), —CF$_3$, or —OCHF$_2$ or such monocyclic and bicyclic rings wherein two or three available carbons have substituents selected from methyl, methoxy, methylthio, halo, —CF$_3$, nitro, hydroxy, amino and —OCHF$_2$.

The term "substituted amino" refers to a group of the formula —NZ$_1$Z$_2$ wherein Z$_1$ is hydrogen, alkyl, cycloalkyl, aryl, arylalkyl, cycloalkylalkyl and Z$_2$ is hydrogen, alkyl, cycloalkyl, aryl, arylalkyl, cycloalkylalkyl, provided that when one of Z$_1$ or Z$_2$ is hydrogen, the other is not hydrogen; or Z$_1$ and Z$_2$ taken together with the nitrogen atom to which they are attached are 1-pyrrolidinyl, 1-piperidinyl, 1-azepinyl, 4-morpholinyl, 4-thiamorpholinyl, 1-piperazinyl, 4-aklyl-1-piperazinyl, 4-arylalkyl-1-piperazinyl, 4-diarylalkyl-1-piperazinyl, 1-pyrrolidinyl, 1-piperidinyl, or 1-azepinyl substituted with alkyl, alkoxy, alkylthio, halo, trifluoromethyl or hydroxy.

In accordance with the present invention, it has been discovered that unexpectedly, certain potassium channel activators have little or no effect on action potential duration (APD) in the heart while retaining the cardioprotective effects as an antiischemic compound and may therefore be used in combination with a class III antiarrhythmic agent to concomitantly treat ischemia and arrhythmia.

Action potential is a response, elicited by stimulus in excitable cells, which is measured from the beginning of membrane depolarization (upstroke) to return to baseline potential (repolarization). Action potential duration is the time interval between the upstroke of the action potential and its point of repolarization. Potassium channel activators having "little effect" on APD in the heart are those which shorten APD while not abolishing the class III antiarrhythmic activity. A preferred group of potassium channel activators having little effect on APD in the heart are those which shorten APD such that the class III antiarrhythmic activity is reduced by less than 50%.

Potassium channel activator having "no effect" on APD in the heart are preferred. Potassium channel activators having no effect on APD in the heart are those which do not reduce the time between the upstroke of the action potential and its point of repolarization and may in fact prolong the time between the upstroke of the action potential and its point of repolarization.

A preferred group of such potassium channel activators which have little or no effect on APD in the heart are the pyranyl cyanoguanidine derivatives.

Examples of preferred pyranyl cyanoguanidine derivatives useful for this invention have the formula I or a pharmaceutically acceptable salt thereof, wherein a, b and d are all carbons or one of a, b and d can be nitrogen or —NO— and the others are carbons;

R$_1$ is

R$_2$ is hydrogen, hydroxy or —OC(O)CH$_3$;

R$_3$ and R$_4$ are each independently hydrogen, alkyl or arylalkyl; or, R$_3$ and R$_4$ taken together with the carbon atom to which they are attached form a 5- to 7-membered carbocyclic ring;

R$_5$ is hydrogen, alkyl, haloalkyl, alkenyl, alkynyl, cycloalkyl, arylalkyl, cycloalkylalkyl, —CN, —NO$_2$, —COR$_{11}$, —COOR$_{11}$, —CONHR$_{11}$, —CON(R$_{11}$)$_2$, —CF$_3$, —S-alkyl, —SOalkyl, —SO$_2$alkyl, halogen, amino, substituted amino, —P(O)(O-alkyl)$_2$, —O-alkyl, —OCF$_3$, —OCH$_2$CF$_3$, —OCOalkyl, —OCONR$_{11}$alkyl, —NR$_{11}$COalkyl, and —NR$_{11}$COOalkyl, —NR$_{11}$CON(R$_{11}$)$_2$ wherein R$_{11}$ in each of the above groups is hydrogen, alkyl, haloalkyl, aryl, arylalkyl, cycloalkyl or (cycloalkyl)alkyl;

R$_6$ is hydrogen, alkyl, —OH, —O-alkyl, amino, substituted amino, —NHCOR$_{11}$ (wherein R$_{11}$ is as defined above), —CN or —NO$_2$;

R$_7$ and R$_8$ are each independently hydrogen, alkyl, alkenyl, aryl, (heterocyclo)alkyl, heterocyclo, arylalkyl, cycloalkyl and (cycloalkyl)alkyl, or alkyl substituted with one or more alkoxy, alkylthio or substituted amino groups; or R$_7$ and R$_8$ taken together with the nitrogen atom to which they are attached form 1-pyrrolidinyl, 1-piperidinyl, 1-azepinyl, 4-morpholinyl, 4-thiamorpholinyl, 1-piperazinyl, 4-alkyl-1-piperazinyl or 4-arylalkyl-1-piperazinyl, wherein each of the so-formed groups can be substituted with alkyl, alkoxy, alkylthio, halogen or trifluoromethyl;

R$_9$ and R$_{10}$ are independently hydrogen, alkyl, alkenyl, aryl, arylalkyl, cycloalkyl or cycloalkylalkyl; or R$_{10}$ can be an aryl group fused to 2 carbon atoms of the cyanoguanidine ring portion; and m is an integer of 1 to 3.

A preferred such pyranyl cyanoguanidine derivative of formula I has the structure:

where R₇ is phenyl or substituted phenyl, with substituted phenyl being preferred and 4-chlorophenyl being most preferred. The potassium channel activators useful for this invention and methods of making such compounds are disclosed in U.S. Pat. No. 5,140,031, issued Aug. 18, 1992 to K. Atwal et. al., which is incorporated by reference herein.

Another example of preferred pyranyl cyanoguanidine compounds are those with the formula II or pharmaceutically acceptable salts thereof wherein a, b and d are as defined for formula I;

Y is a single bond, —CH₂—, —C(O)—, —O—, —S— or —N(R₁₉)—;

R₁₂ is aryl or heterocyclo;

R₁₃ is —COOR₁₉, —CO-amino, —CO-substituted amino, amino, substituted amino, —NR₁₉CO-amino, —NR₁₉CO-substituted amino, —NR₁₉COR₂₀, —NR₁₉SO₂R₂₀, —NR₁₉(C=NCN)-amino, —NR₁₉(C=NCN)-substituted amino, —SR₁₉, —SOR₁₉, —SO₂R₁₉, —OR₁₉, cyano, heterocyclo, pyridine-N-oxide, —CH(OR₁₉)₂, (where Z is O or H₂) or $$\begin{matrix} NR_{19}R_{20} & O \\ | & || \\ -C=CH-C-R_{19}; \end{matrix}$$

R₁₄ is hydrogen, hydroxy or —OC(O)R₁₉;

R₁₅ and R₁₆ are each independently hydrogen, alkyl or arylalkyl, or R₁₅ and R₁₆ taken together with the carbon atom to which they are attached form a 5- to 7-membered carbocyclic ring;

R₁₇ is hydrogen, alkyl, haloalkyl, alkenyl, alkynyl, cycloalkyl, arylalkyl, (cycloalkyl)alkyl, —CN, —NO₂, —COR₁₉, —COOR₁₉, —CONHR₁₉, —CONR₁₉R₂₀, —CF₃, —S-alkyl, —SOalkyl, —SO₂alkyl, —P(O)(O-alkyl)₂, $$\begin{matrix} O & O \\ || & / \\ -P & \\ & \\ O & ])_n \end{matrix} R_{19},$$

halogen, amino, substituted amino, —O-alkyl, —OCF₃, —OCH₂CF₃, —OCOalkyl, —OCONR₁₉alkyl, —NR₁₉COalkyl, —NR₁₉COOalkyl or —NR₁₉CONR₂₀, tetrazolyl, imidazole, oxazole or triazole;

R₁₈ is hydrogen, alkyl, hydroxy, —O-alkyl, amino, substituted amino, —NHCOR₁₉, —CN or —NO₂;

R₁₉ and R₂₀ are independently hydrogen, alkyl, haloalkyl, aryl, arylalkyl, cycloalkyl or (cycloalkyl)alkyl;

X is alkyl; or X—R₁₃ together can be hydrogen, aryl or heterocyclo when R₁₂ is heterocyclo; and n is an integer of 1 to 3.

Class III antiarrhythmic agents are a well known class of agents. Preferred examples for use in accordance with this invention are:

A. Dofetilide, which has the chemical name: N-[4-[2-[methyl[2-4-[(methylsulfonyl)amino]phenoxy]ethyl]-phenyl]-methanesulfonamide and the structure:

This compound and methods for preparing this compound are disclosed in U.S. Pat. No. 4,959,366, issued Sep. 25, 1990;

B. Risotilide, which has the chemical name: N-(1-methylethyl)-N-[2-[(1-methylethyl)amino]ethyl]-4-(methylsulfonyl)-amino]-benzenesulfonamide and the structure:

This compound and methods for preparing this compound are disclosed in U.S. Pat. No. 4,721,809, issued Jan. 26, 1988;

C. A compound having the structure:

This compound and method for preparing this compound are disclosed in EP 431944, published Jun. 12, 1991;

D. A compound having the structure:

This compound and method for preparing this compound are disclosed in EP 431945, published Jun. 12, 1991;

E. A compound having the structure:

This compound and method for preparing this compound are disclosed in EP 431943, published Jun. 12, 1991;

F. Almokalant, which has the chemical name: 4-(3-(ethyl (3-(propylsulfinyl)propyl)amino)-2-hydroxypropoxy)-benzonitrile and the structure:

This compound and methods for preparing this compound are disclosed in U.S. Pat. No. 5,034,411, issued Jul. 23, 1991;

G. E 4031, which has the chemical name: Methanesulfonanilide, N-[4-[[1-[2-(6-methyl-2-pyridinyl)ethyl]-4-piperidinyl]carbonyl]phenyl]-(9CI) and the structure:

This compound and methods for preparing this compound are disclosed in U.S. Pat. Nos. 4,876,262, issued Oct. 24, 1989 and 4,996,215, issued Feb. 26, 1991;

H. Ibutilide fumarate, which has the chemical name: N-[4-[1-Hydroxy-2-[(1-methylethyl)amino]ethyl] phenyl]-methanesulfonamide, monohydrochloride, and the structure:

This compound and methods for preparing this compound are disclosed in U.S. Pat. No. 5,155,268;

I. NE-10064, has the chemical name: (E)-1-[[[5-(4-Chlorophenyl)-2-furanyl]methylene]amino]-3-[4-(4-methyl-1-piperazinyl)butyl]-2,4-imidazolidine-dione, and the structure:

This compound and methods for preparing this compound are disclosed in European Patent Application 598,061, published May 25, 1994; and J. Sotolol and d-sotolol, which has the chemical name: 4-(2-isopropylamino-1hydroxyethyl)-methanesulfonanilide, and the structure:

These compounds and methods for preparing these compounds are disclosed in U.S. Pat. Nos. 3,341,584 and 5,089,526.

The disclosures of all of the above cited patents and/or applications are incorporated by reference herein.

In carrying out the method of the present invention, potassium channel openers and class III antiarrhythmic compounds may be co-administered to mammalian species, such as monkeys, dogs, cats, rats, humans, etc. and as such may be independently incorporated in a conventional systemic dosage form, such as a tablet, capsule, elixir and injectable or combined in a conventional systemic dosage form. The above dosage forms will also include the necessary carrier material, excipient, lubricant, buffer, antibacterial, bulking agent (such as mannitol), anti-oxidants (ascorbic acid or sodium bisulfite) or the like. Oral dosage forms are preferred, although parenteral forms are quite satisfactory as well.

The dose administered must be carefully adjusted according to age, weight and condition of the patient, as well as the route of administration, dosage form and regimen and the desired result. In addition, the dose actual dose will depend on the specific compounds selected.

Thus for oral administration, a satisfactory result may be obtained employing the potassium channel opener in an amount from about 0.01 mg/kg to about 100 mg/kg and preferably from about 1 mg/kg to about 10 mg/kg. The dose of the class III antiarrhythmic compound is dependent on the particular compound to be used. Suitable dosages for the preferred compounds are disclosed in the patents cited above. Generally, a suitable dose may be between about 0.01 mg/kg to about 100 mg/kg and preferably from about 0.1 mg/kg to about 25 mg/kg for oral administration.

The co-administration described above may be accomplished in the dosage forms as described above in single or divided doses of one to four times daily. It may be advisable to start a patient on low doses and work up gradually to high doses.

Tablets of various sizes can be prepared, e.g., of about 5 to 700 mg in total weight, containing the active substance or substances in the ranges described above, with the remainder being a physiologically acceptable carrier of other materials according to accepted pharmaceutical practice. These tablets can, of course, be scored to provide for fractional doses. Gelatin capsules can be similarly formulated.

Liquid formulations can also be prepared by dissolving or suspending the active substance or substances in a conventional liquid vehicle acceptable for pharmaceutical administration so as to provide the desired dosages in one to four teaspoonfuls.

Such dosage forms can be administered to the patient on a regimen of one to four doses per day.

Illustrative of the adjuvants which may be incorporated in tablets are the following: a binder such as gum tragacanth, acacia, corn starch or gelatin; an excipient such as dicalcium phosphate or cellulose; a disintegrating agent such as corn starch, potato starch, alginic acid or the like; a lubricant such as stearic acid or magnesium stearate; a sweetening agent such as sucrose, lactose or saccharin; a flavoring agent such as orange, peppermint, oil of wintergreen or cherry. When the dosage unit form is a capsule, it may contain in addition to materials of the above type a liquid carrier such as a fatty oil. Various other materials may be present as coatings or to otherwise modify the physical form of the dose unit. For instance, tablets or capsules may be coated with shellac, sugar or both. A syrup of elixir may contain the active compound, water, alcohol or the like as the carrier, glycerol as solubilizer, sucrose as sweetening agent, methyl and propyl parabens as preservatives, a dye and a flavoring such as cherry or orange.

According to another modification, in order to more finely regulate the dosage schedule, the active substances may be administered separately in individual dosage units at the same time or carefully coordinated times. Since blood levels are built up and maintained by a regulated schedule of administration, the same result is achieved by the simultaneous presence of the two substances. The respective substances can be individually formulated in separate unit dosage forms as described above.

Fixed combinations of a potassium channel opener and a class III antiarrhythmic compound are more convenient and are preferred, especially in tablet or capsule form for oral administration. In addition, it is also within the scope of this invention that one or more potassium channel openers can be combined with one or more class III antiarrhythmic compound.

In formulating the compositions, the active substances, in the amounts described above, are compounded according to accepted pharmaceutical practice with a physiologically acceptable vehicle, carrier, excipient, binder, preservative, stabilizer, flavor, etc., in the particular type of unit dosage form.

The active substances described above form commonly known, pharmaceutically acceptable salts such as alkali metal and other common basic salts or acid addition salts, etc. References to these substances are therefore intended to include those common salts known to be substantially equivalent to the present compound.

Sustained release forms of such formulations which may provide such amounts biweekly, weekly, monthly and the like may also be employed. A dosing period of at least one to two weeks are required to achieve minimal benefit.

The following examples and preparations describe the manner and process of making and using the preferred embodiments of the invention and are illustrative rather than limiting. It should be understood that there may be other embodiments which fall within the spirit and scope of the invention as defined by the claims appended hereto.

EXAMPLE 1

The following experiment was carried out to demonstrate that the potassium channel activators in accordance with the invention are antiischemic but have little or no effect on action potential duration in the heart and thus may be used in combination with a class III antiarrhythmic agent to concomitantly treat ischemia and arrhythmia.

Methods

Effects of Cromakalim and Compound A on Severity of Ischemia in Guinea Pig Hearts Guinea pigs of both sexes (400–500 g) were anesthetized using 100 mg/kg sodium pentobarbital (i.p.). The trachea was intubated and then the jugular vein was injected with heparin (1000 U/kg). While being mechanically ventilated, their hearts were perfused in situ via retrograde cannulation of the aorta. The hearts were then excised and quickly moved to a Langendorff apparatus where they were perfused with oxygenated Krebs-Henseleit solution containing (in mM): 112 NaCl, 25 NaHCO$_3$, 5 KCl, 1.2 MgSO$_4$, 1 KH$_2$PO$_4$, 2.5 CaCl$_2$, 11.5 glucose and 2 pyruvate at a constant perfusion pressure (85 mm Hg). A water-filled latex balloon was attached to a metal cannula and was then placed into the left ventricle and connected to a Statham pressure transducer (Gould Inc Oxnard, Calif.) for measurement of left ventricular pressure. The hearts were allowed to equilibrate for 15 minutes, at which time end diastolic pressure (EDP) was adjusted to 5 mm Hg using the latex balloon. This balloon volume was then maintained for the duration of the experiment. Pre-ischemia or pre-drug function, heart rate and coronary flow (extracorporeal electromagnetic flow probe, Carolina Medical Electronics, King, N.C.) were then measured. Contractile function was calculated by subtracting left ventricular peak systolic pressure from EDP, giving left ventricular developed pressure (LVDP). Cardiac temperature was maintained throughout the study by submerging the hearts in 37° C. buffer which was allowed to accumulate in a heated chamber.

Once baseline cardiac function and coronary flow data were obtained, the drug perfusions were begun. In the first study, guinea pig hearts were given vehicle (0.04% DMSO, n=4), 1–10 μM cromakalim (n=4 per concentration), or 1–10 μM compound A (n=4 per concentration). The respective drug or vehicle was administered with the perfusate for 10 minutes before the onset of global ischemia. Global ischemia was instituted by completely shutting off the perfusate flow. EDP was followed during the course of global ischemia and the time to the onset of contracture recorded. Time to contracture was defined as the time necessary for the first 5 mm Hg increase in EDP. Cardioprotective potency was then calculated as the concentration (μM) necessary for a 25% increase (from vehicle values) in time to contracture and was designated as EC$_{25}$. This index of cardioprotective potency is an accepted reliable means of comparing activity for agents such as K$_{ATP}$ channel openers.

Additional studies in a guinea pig heart model of ischemia and reperfusion were conducted and the effect of glyburide on the activity of cromakalim and compound A was determined. After equilibration, the hearts were subjected to one of several treatments. Hearts were treated with vehicle (0.04%DMSO, n=5), 10 μM compound A (n=5), 10 μM cromakalim (n=5), 0.3 μM glyburide (n=5), 10 μM compound A+0.3 μM glyburide (n=5), or 10 μM cromakalim+0.3 μM glyburide (n=5). The respective drug treatments were given for 10 minutes and were included in the perfusate. At this time, the hearts were subjected to 45 minutes global ischemia and 30 minutes reperfusion. Ischemia was initiated by completely shutting off perfusate flow. At the end of the reperfusion period, contractile function, coronary flow, and LDH release were measured as previously described. The respective drugs were given only before global ischemia and were not given during reperfusion.

Microelectrode Recording Techniques in Guinea Pig Papillary Muscle

Male guinea pigs (450–600 g) were sacrificed by cervical dislocation. Hearts were rapidly removed, and rinsed in Krebs-Henseleit bicarbonate buffer solution (room temperature) equilibrated with 95% O$_2$/5% CO$_2$. The buffer was composed of the following (mM): 112 NaCl, 5.0 KCl, 11.5 glucose, 25 NaHCO$_3$, 1.2 MgSO$_4$, 1.25 CaCl$_2$, 5.0 mM HEPES, 1.0 KH$_2$PO$_4$ at a pH 7.4. A posterior papillary muscle, 3–5 mm in length and 1 mm or less in diameter, was removed from the right or left ventricle and was pinned to the base of a 5 mL tissue chamber. The papillary muscle was continuously stimulated through a pair of platinum wires with 1-msec square wave pulses set at 200% of threshold voltage. The frequency of stimulation was held constant at 6 Hz during the first hour of equilibration, and then paced at 1 Hz during the remaining equilibration period. Muscles were allowed 2–3 hr to equilibrate while being superfused with oxygenated Krebs-Henseleit solution (15–25 ml/min at 37±0.2° C.).

Standard microelectrode techniques were employed to impale single myocardial cells in a multicellular preparation and to record transmembrane action potentials. Microelectrodes were filled with a solution containing 3 M KCl, 500 μM EDTA and 10 mM HEPES, electrodes with tip resistances of 10–20 MΩ were coupled to an amplifier (Axoclamp-2A; Axon Instruments, Burlingame Calif.). Electrical potentials were displayed on a digital oscilloscope (Yokogawa model D1200; Newnan, Ga.). Signals were recorded on a chart recorder (Gould model 2400S) and analyzed with a computer using the digital data obtained from the oscilloscope.

Following equilibration, transmembrane action potentials were recorded and resting membrane potentials, amplitudes, maximum upstroke velocity (Vmax) and durations at 20%, 50% and 90% levels of repolarization (APD$_{20}$, APD$_{50}$, and APD$_{90}$) were measured at a stimulating frequency of 2 Hz. Either vehicle (DMSO; volume equivalence, n=8) compound A (10, 30 or 100 μM, n=6,7,8 respectively) or cromakalim (10 μM, n=5) were added to the buffer solution, and tissues allowed 30 minutes for equilibration. Action potential measurements were repeated. At this time, tissues were exposed to an hypoxic solution of Krebs-Henseleit (buffer bubbled with 95% N$_2$/5% CO$_2$ for 15 minutes either containing vehicle, compound A or cromakalim. Action potential parameters were measured at 1, 3, 5, 7, 9, 11, 13, and 15 minutes of hypoxia. Oxygenated Krebs-Henseleit solution containing the appropriate compounds was returned to the bath (re-oxygenation) and action potentials measured at 3, 5, 7, 9, 11, 15, 20, 25, and 30 minutes. All drugs were dissolved in dimethyl sulfoxide (DMSO; Sigma St. Louis, Mo.). Drugs were dissolved to give no greater than a 0.1% concentration of DMSO.

Electrophysiologic Determinations in Isolated Perfused Heart Preparations

Guinea pigs were anesthetized and hearts removed as described above. Hearts were quickly connected to a Langendorff apparatus where they were perfused with oxygenated Krebs-Henseleit solution containing in (mM): 112 NaCl, 5.0 KCl, 11.5 glucose, 25 NaHCO$_3$, 1.2 MgSO$_4$, 1.25 CaCl$_2$, and 1.0 KH$_2$PO$_4$ at a pH 7.4. Hearts were perfused horizontally with Krebs-Henseleit buffer at a constant pressure (85 mmHg) and temperature (37° C.).

Atria were removed and hearts instrumented with a surface electrode (Inapres, Norwich N.Y.) and ECG leads. The surface electrode was used for pacing. ECG as well as an epicardial monophasic action potential (MAP; Franz epicardial Langendorff probe; EP Technologies, Sunnyvale, Calif.) were continuously recorded throughout the experiment. ECG and MAP signals were routed to a chart recorder TA4000; Gould, Cleveland Ohio) and oscilloscope (DL1200; Yokogawa, Newnan Ga.). The ambient temperature around the preparation was maintained by a heated vessel (37° C.; FE 3; Haake, Germany).

Electrophysiologic measurements were made twice before drug administration, and following sequential administration of test substances. Determinations of action potential duration at the 90% repolarization level were made from the plateau region of the MAP, and QT-intervals were determined at a ventricular pacing rate of 4 Hz with single pulses of 2-msec duration at twice the threshold current.

Each heart was given 20 minutes equilibration time. Following equilibration, two control electrophysiologic readings were taken. Hearts were then given vehicle (0.1% DMSO), cromakalim (10 μm) or compound A (10 μm). At the end of 10 minutes of compound administration, electrophysiologic determinations were repeated. At this time, tissues were exposed to an hypoxic solution of Krebs-Henseleit (buffer bubbled with 95% $N_2$/5% $CO_2$) for seven minutes and measurements repeated.

Statistics

Differences with respect to time and treatment were discerned using a factorial analyis of variance. A Newman-Keuls post-hoc test was used to determine precise differences. All values were expressed as mean±standard error. Significance was set at a p value <0.05.

Results

Figure 1:
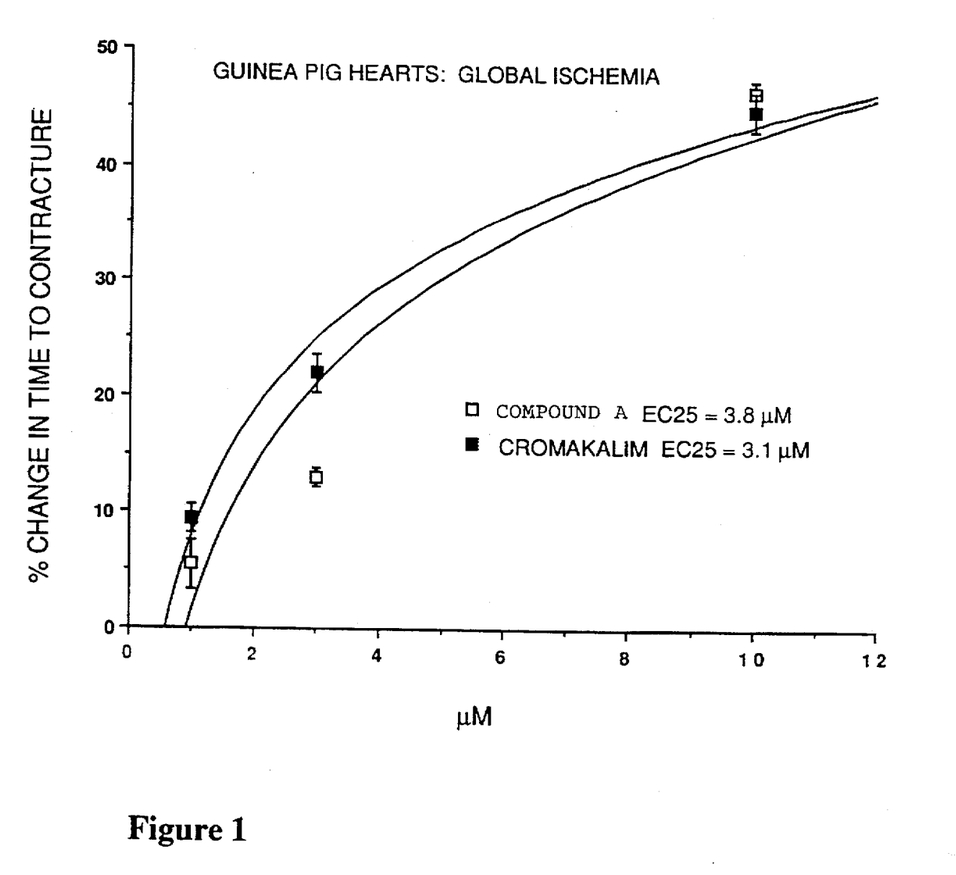
FIG. 1 shows the effect of compound A and cromakalim (in increasing concentrations) on time to contracture in globally ischemic guinea pig hearts. The data is expressed as the percent change in time to contracture from vehicle-treated group values.

Effects of Cromakalim and Compound A on Severity of Ischemia in Guinea Pig Hearts In order to show that the cardioprotective potencies in guinea pig hearts were similar for cromakalim and compound A, $EC_{25}$ for increasing time to contracture was calculated. $EC_{25}$ is calculated from these data and is defined as the concentration (μM) in which a 25% increase in time to contracture is observed, relative to vehicle treated hearts. The data is shown in FIG. 1 as the percent change in time to contracture from vehicle group values. As can be seen in this figure, the effects of cromakalim and compound A on time to contracture were nearly identical. The $EC_{25}$ for cromakalim was 3.1 and for compound A was 3.8 μM. The absolute time to contracture was 30.4±0.3 min in the vehicle treated group.

A more detailed study on the effects of cromakalim and compound A on the severity of ischemia was conducted, with and without glyburide. The determination of the time to contracture-concentration curves for cromakalim and compound A indicated that 10 μM concentrations of these compounds should yield significant and similar cardioprotective effects. The effects of 10 μM cromakalim and compound A on pre- and post-ischemic contractile function and coronary flow in isolated guinea pig hearts are shown in Table 1.

TABLE 1

|  | Predrug | Postdrug | Reper 30 Min. |
|---|---|---|---|
| Heart Rate (Beats/min) | | | |
| Vehicle | 225 ± 12 | 222 ± 10 | 189 ± 35 |
| Cromakalim | 215 ± 5 | 204 ± 4 | 219 ± 4 |
| Compound A | 200 ± 9 | 189 ± 11 | 200 ± 10 |
| 0.3 μM Glyburide | 217 ± 4 | 209 ± 4 | 200 ± 11 |
| Crom + Glyburide | 222 ± 8 | 204 ± 5 | 201 ± 8 |
| A + Glyburide | 213 ± 9 | 189 ± 6 | 208 ± 14 |

TABLE 1-continued

|  | Predrug | Postdrug | Reper 30 Min. |
|---|---|---|---|
| LVDP (mm Hg) | | | |
| Vehicle | 101 ± 11 | 91 ± 8 | 8 ± 2[a] |
| Cromakalim | 94 ± 3 | 69 ± 5[a,b] | 33 ± 5[a,b] |
| Compound A | 94 ± 12 | 69 ± 6[a,b] | 41 ± 2[a,b] |
| 0.3 μM Glyburide | 106 ± 2 | 96 ± 2 | 7 ± 1[a] |
| Crom + Glyburide | 90 ± 11 | 77 ± 7 | 11 ± 1[a] |
| A + Glyburide | 100 ± 5 | 70 ± 5[a,b] | 12 ± 3[a] |
| Coronary Flow (ml/min/g) | | | |
| Vehicle | 28 ± 4 | 29 ± 2 | 17 ± 3[a] |
| Cromakalim | 27 ± 2 | 34 ± 1[a] | 19 ± 3 |
| Compound A | 28 ± 3 | 28 ± 2 | 18 ± 4 |
| 0.3μ M Glyburide | 27 ± 2 | 28 ± 3 | 7 ± 1[a,b] |
| Crom + Glyburide | 27 ± 2 | 28 ± 1 | 12 ± 3[a] |
| A + Glyburide | 26 ± 2 | 26 ± 3 | 12 ± 3[a] |

All values are mean ± SE; LVDP = left ventricular developed pressure, n = 5 per group
[a]Significantly different from its respective predrug value (p < 0.05).
[b]Significantly different from its respective vehicle group value (p < 0.05).

Both cromakalim and compound A exerted significant, although moderate negative inotropic effects at 10 μM in nonischemic guinea pig hearts. Cromakalim significantly increased coronary flow while compound A was without effect. Neither drug affected heart rate. Glyburide had no significant effect on pre-ischemic cardiac function or heart rate. It also had no effect on pre-ischemic coronary flow. Glyburide had no effect on the pre-ischemic negative inotropic activity of cromakalim or compound A, but did abolish the coronary dilator effect of cromakalim. After 45 minutes global ischemia, reperfusion LVDP (30 minutes into reperfusion) was significantly attenuated from pre-ischemic values in vehicle treated hearts. A moderate degree of bradycardia was also observed at this time, although it did not achieve statistical significance. Both cromakalim and compound A significantly enhanced the reperfusion recovery of contractile function compared to vehicle treated hearts. The protective effects of cromakalim and compound A on reperfusion LVDP were abolished by glyburide. Glyburide alone appeared to reduce the reperfusion coronary flow response, an effect which was attenuated in the presence of the $K_{ATP}$ openers.

Figure 2:
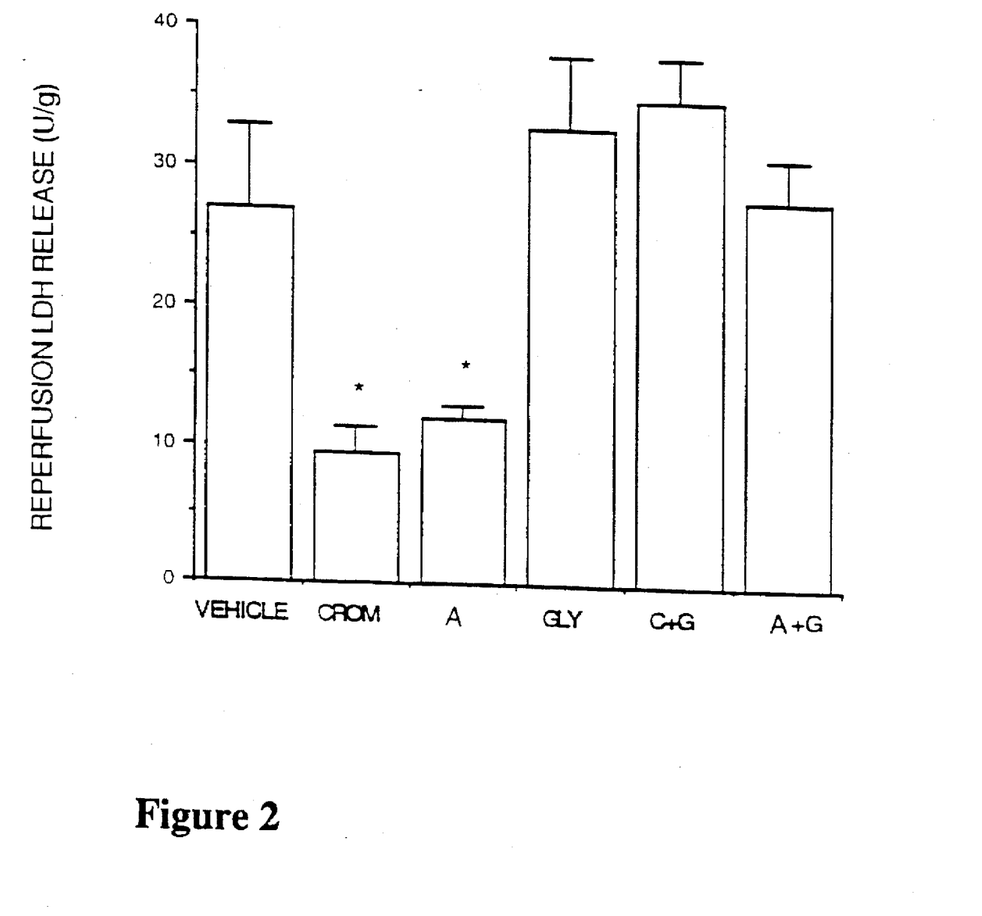
FIG. 2 shows the effect of 10 µM cromakalim (CROM or C) and compound A (A) on cumulative LDH release following 45 minutes global ischemia in isolated guinea pig hearts. Cromakalim and compound A both significantly reduced LDH release during reperfusion. Glyburide (GLY) alone at 0.3 µM had no effect on this parameter, but completely abolished the protective effects of both compound A and cromakalim.
Figure 3:
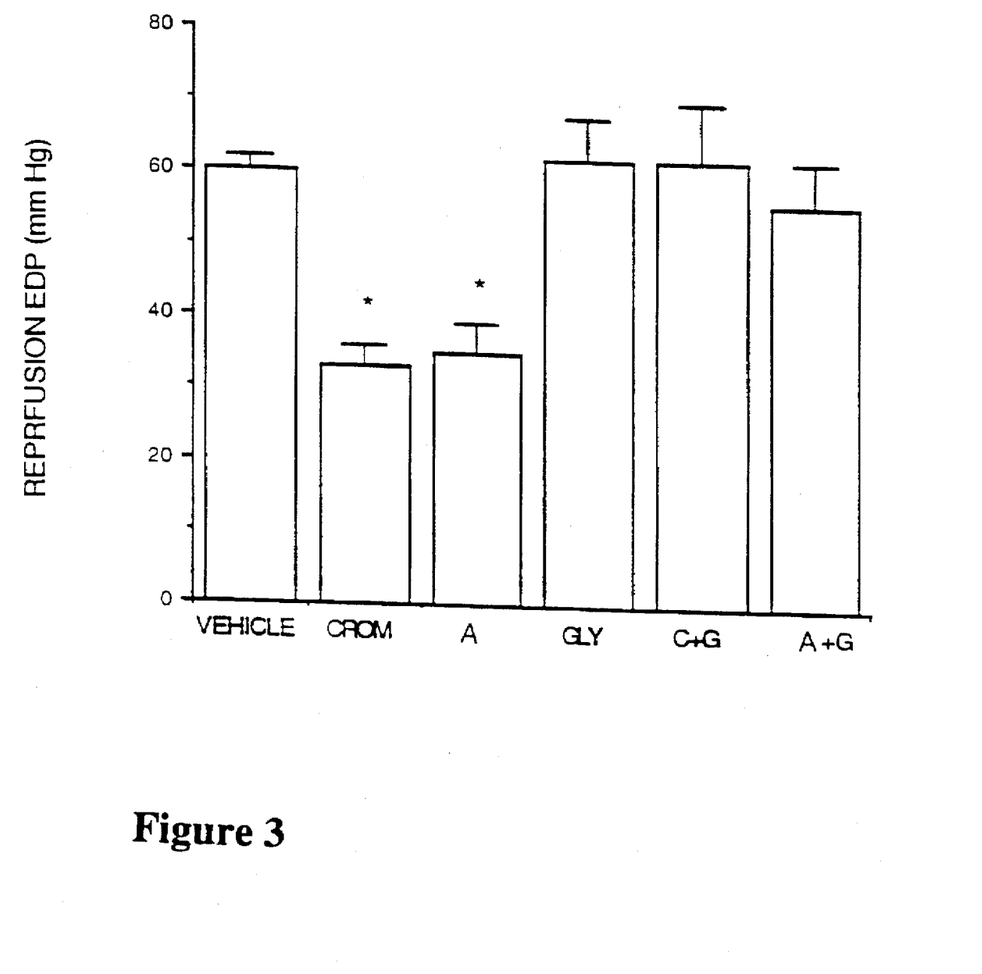
FIG. 3 shows the effect of 10 µM cromakalim (CROM or C) or compound A (A) on reperfusion end-diastolic pressure (EDP) following 45 minutes global ischemia in isolated guinea pig hearts. Cromakalim and compound A both significantly reduced EDP during reperfusion. Glyburide (GLY) alone at 0.3 µM had no effect on this parameter, but completely abolished the protective effects of both compound A and cromakalim.

The effect of cromakalim and compound A on reperfusion LDH release and reperfusion EDP are shown in FIGS. 2 and 3 respectively. Significant LDH release was observed in vehicle treated hearts as well as reperfusion contracture. LDH release was significantly (*, P<0.05) attenuated by cromakalim and compound A at 10 μM. Similar results were also observed for EDP. Glyburide alone had no effect on either parameter, but completely abolished the protective effects of the $K_{ATP}$ openers. For cromakalim, the combination with glyburide was slightly pro-ischemic.

Figure 4:
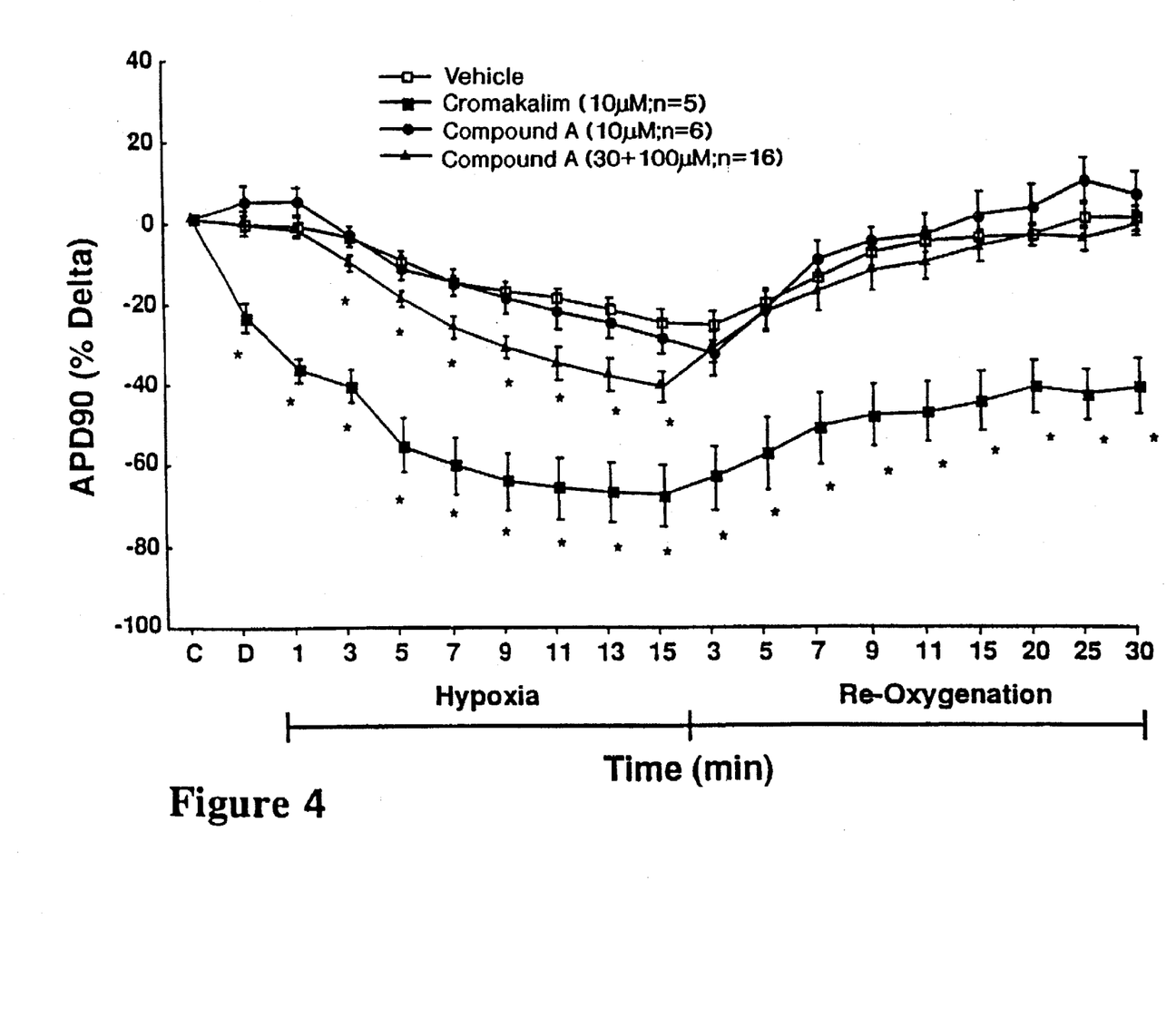
FIG. 4 shows the effects of vehicle (0.1% DMSO), cromakalim (10 µM), or compound A (10 µM) or pooled values for 30 and 100 µM on action potential durations at 90% repolarization ($APD_{90}$). The data are expressed as a percent change from control. Measurements were taken at control (C) and after drug (D) administration, and at set time periods during 15 minutes of hypoxia and for 30 minutes following re-oxygenation. Compound A did not significantly change action potential characteristics under normoxic conditions. During hypoxia, compound A (10 µM) did not significantly alter $APD_{90}$ values relative to vehicle.

Intracellular Recording of the Cardiac Action Potential in Isolated Guinea Pig Papillary Muscle Guinea pig papillary muscle treated with vehicle alone displayed no change in action potential characteristics under normoxic conditions. In the presence of hypoxia, a slight but nonsignificant reduction in Vmax, $APD_{20}$, $APD_{50}$ and $APD_{90}$ was observed. Values returned to control levels during the reperfusion or re-oxygenation period. Compound A at 10, 30 or 100 μM did not significantly change action potential characteristics under normoxic conditions. *Significantly different (P<0.05) from corresponding vehicle values. At concentrations of 30 and 100 μM, compound A produced identical effects on action potential characteristics. Therefore, the values for these two doses were pooled. During hypoxia, compound A (10 μM) did not significantly alter $APD_{90}$ values relative to vehicle (FIG. 4). $APD_{90}$ values decreased approximately 20% to 26% in the vehicle treated muscles compared with 22% to 29% in the compound A treated muscles at 11 to 15 min of hypoxia. At 30–100 μM, compound A significantly reduced $APD_{90}$ values by 36% to 42% at 11 to 15 min of hypoxia. In contrast, cromakalim (10 μM) significantly reduced $APD_{90}$ values under normoxic conditions. $APD_{90}$ values were decreased from 140±9 to 105±9 msec (25%). During hypoxia, cromakalim reduced $APD_{90}$ values 66% to 67% at 11 to 15 min of hypoxia. Following re-oxygenation electrophysiologic parameters for both vehicle treated and compound A treated muscles returned to control levels. $APD_{90}$ values in the cromakalim treated muscles returned to post-drug levels during the re-oxygenation period. There were no significant changes in resting membrane potential, action potential overshoots or Vmax in either the compound A or cromakalim treatment groups under normoxic conditions. During hypoxia compound A (30 to 100 μM) and cromakalim (10 μM) caused a slight, but significant reduction in resting potential (from 89±1 to 84±1 mV and from 91±2 to 86±1 mV, respectively), which quickly recovered on reoxygenation. There were no significant changes in action potential overshoots or Vmax in either the compound A or cromakalim treatment groups during hypoxia.

Epicardial Recording of the Cardiac Action Potential and Measurement of the QT-Interval in Isolated Perfused Guinea Pig Hearts Isolated perfused guinea pig heart demonstrated no significant differences in $APD_{90}$ or QT-interval at control readings. Following administration of cromakalim (10 μm) there was a significant reduction in $APD_{90}$ and QT-interval of 16±2% and 11±2%, respectively. Table 2, below shows the effect of vehicle (0.1% DMSO), cromakalim (10 μM) and compound A (10 μM) on hypoxia-induced changes in action potential durations at 90% repolarization ($APD_{90}$; msec) and QT-intervals (msec) in the isolated perfused guinea pig heart at a stimulation rate of 4 Hz.

TABLE 2

| Drug | n | Control $APD_{90}$ | QT | Post Drug $APD_{90}$ | QT | Hupoxia $APD_{90}$ | QT |
|---|---|---|---|---|---|---|---|
| Vehicle | 6 | 123± 1 | 138 ± 2 | 127 ± 2 | 142 ± 1 | 92 ± 2cv | 99 ± 3c |
| Cromakalim | 6 | 126 ± 3 | 142 ± 1 | 106 ± 3cv | 126 ± 2cv | 43 ± 5cv | 60 ± 3cv |
| Compound A | 6 | 122 ± 1 | 137 ± 1 | 132 ± 2c | 52 ± 3cv | 94 ± 2c | 109 ± 2cv |

\* - Values taken following 7 minutes of hypoxia.
c - Significantly different (p < 0.05) from corresponding control values.
v - Significantly different (p < 0.05) from corresponding vehicle values.

These changes were also significantly different than vehicle-treated hearts. In contrast, compound A cause a slight but significant increase in $APD_{90}$ or QT-interval values of 9±2% and 11±2%, respectively. Under hypoxic conditions, vehicle-treated hearts displayed a 25±3% and 28±2% decrease in $APD_{90}$ or QT-interval, respectively. Cromakalim caused a precipitous decrease in $APD_{90}$ or QT-interval values during hypoxia of 66±2% and 58±2%, respectively. Unlike cromakalim compound A caused a reduction in $APD_{90}$ (22±1%) and QT-interval (21±2%) values that was similar to that observed in vehicle-treated hearts.

What is claimed is:

1. A method for concomitantly treating ischemia and arrhythmia in a mammalian specie, which comprises co-administering to a mammalian specie in need thereof an effective ischemia treating amount of a potassium channel opener having little or no effect on action potential duration in the heart and an effective arrhythmia treating amount of a class III antiarrhythmic compound.

2. The method as recited in claim 1 wherein the potassium channel opener is a compound of formula I or a pharmaceutically acceptable salt thereof, wherein a, b and d are all carbons or one of a, b and d can be nitrogen or —NO— and the others are carbons;

$R_1$ is $R_2$ is hydrogen, hydroxy or —OC(O)CH$_3$;

$R_3$ and $R_4$ are each independently hydrogen, alkyl or arylalkyl; or, $R_3$ and $R_4$ taken together with the carbon atom to which they are attached form a 5- to 7-membered carbocyclic ring;

$R_5$ is hydrogen, alkyl, haloalkyl, alkenyl, alkynyl, cycloalkyl, arylalkyl, cycloalkylalkyl, —CN, —NO$_2$, —COR$_{11}$, —COOR$_{11}$, —CONHR$_{11}$, —CON(R$_{11}$)$_2$, —CF$_3$, —S-alkyl, —SOalkyl, —SO$_2$alkyl, halogen, amino, substituted amino, —P(O)(O-alkyl)$_2$, —O-alkyl, —OCF$_3$, —OCH$_2$CF$_3$, —OCOalkyl, —OCONR$_{11}$alkyl, —NR$_{11}$COalkyl, and —NR$_{11}$COOalkyl, —NR$_{11}$CON(R$_{11}$)$_2$ wherein R$_{11}$ in each of the above groups is hydrogen, alkyl, haloalkyl, aryl, arylalkyl, cycloalkyl or (cycloalkyl)alkyl;

$R_6$ is hydrogen, alkyl, —OH, —O-alkyl, amino, substituted amino, —NHCOR$_{11}$ (wherein R$_{11}$ is as defined above), —CN or —NO$_2$;

$R_7$ and $R_8$ are each independently hydrogen, alkyl, alkenyl, aryl, (heterocyclo)alkyl, heterocyclo, arylalkyl, cycloalkyl and (cycloalkyl)alkyl, or alkyl substituted with one or more alkoxy, alkylthio or substituted amino groups; or R$_7$ and R$_8$ taken together with the nitrogen atom to which they are attached form 1-pyrrolidinyl, 1-piperidinyl, 1-azepinyl, 4-morpholinyl, 4-thiamorpholinyl, 1-piperazinyl, 4-alkyl-1-piperazinyl or 4-arylalkyl-1-piperazinyl, wherein each of the so-formed groups can be substituted with alkyl, alkoxy, alkylthio, halogen or trifluoromethyl;

$R_9$ and $R_{10}$ are independently hydrogen, alkyl, alkenyl, aryl, arylalkyl, cycloalkyl or cycloalkylalkyl; or R$_{10}$ can be an aryl group fused to 2 carbon atoms of the cyanoguanidine ring portion; and m is an integer of 1 to 3; or a compound of the formula II or pharmaceutically acceptable salts thereof wherein
a, b and d are as defined above;
Y is a single bond, —CH$_2$—, —C(O)—, —O—, —S— or —N(R$_{19}$)—;
$R_{12}$ is aryl or heterocyclo;
$R_{13}$ is —COOR$_{19}$, —CO-amino, —CO-substituted amino, amino, substituted amino, —NR$_{19}$CO-amino, —NR$_{19}$CO-substituted amino, —NR$_{19}$COR$_{20}$, —NR$_{19}$SO$_2$R$_{20}$, —NR$_{19}$(C=NCN)-amino, —NR$_{19}$(C=NCN)-substituted amino,

—SR$_{19}$, —SOR$_{19}$, —SO$_2$R$_{19}$, —OR$_{19}$, cyano, heterocyclo, pyridine-N-oxide, —CH(OR$_{19}$)$_2$,

(where Z is O or H$_2$) or $R_{14}$ is hydrogen, hydroxy or —OC(O)R$_{19}$;

$R_{15}$ and $R_{16}$ are each independently hydrogen, alkyl or arylalkyl, or R$_{15}$ and R$_{16}$ taken together with the carbon atom to which they are attached form a 5- to 7-membered carbocyclic ring;

$R_{17}$ is hydrogen, alkyl, haloalkyl, alkenyl, alkynyl, cycloalkyl, arylalkyl, (cycloalkyl)alkyl, —CN, —NO$_2$, —COR$_{19}$, —COOR$_{19}$, —CONHR$_{19}$, —CONR$_{19}$R$_{20}$, —CF$_3$, —S-alkyl, —SOalkyl, —SO$_2$alkyl, —P(O)(O-alkyl)$_2$, halogen, amino, substituted amino, —O-alkyl, —OCF$_3$, —OCH$_2$CF$_3$, —OCOalkyl, —OCONR$_{19}$alkyl, —NR$_{19}$COalkyl, —NR$_{19}$COOalkyl or —NR$_{19}$CONR$_{20}$, tetrazolyl, imidazole, oxazole or triazole;

$R_{18}$ is hydrogen, alkyl, hydroxy, —O-alkyl, amino, substituted amino, —NHCOR$_{19}$, —CN or —NO$_2$;

$R_{19}$ and $R_{20}$ are independently hydrogen, alkyl, haloalkyl, aryl, arylalkyl, cycloalkyl or (cycloalkyl)alkyl;

X is alkyl; or X—R$_{13}$ together can be hydrogen, aryl or heterocyclo when R$_{12}$ is heterocyclo; and n is an integer of 1 to 3.

3. The method as recited in claim 1 wherein the potassium channel opener is a compound of formula where R$_{13}$ is phenyl or substituted phenyl.

4. The method as recited in claim 1 wherein the potassium channel opener is a compound of formula 5. The method as recited in claim 1 wherein the class III antiarrhythmic compound is:

N-[4-[2-[methyl[2-4-[(methylsulfonyl)amino]-phenoxy]ethyl]-phenyl]-methanesulfonamide;

N-(1-methylethyl)-N-[2-[(1-methylethyl)amino]ethyl]-4-(methylsulfonyl)-amino]-benzenesulfonamide;

a compound having the structure:

a compound having the structure:

a compound having the structure:

4-(3-(ethyl(3-(propylsulfinyl)propyl)-amino)-2-hydroxypropoxy)-benzonitrile;

methanesulfonanilide, N-[4-[[1-[2-(6-methyl-2-pyridinyl)ethyl]-4-piperidinyl]carbonyl]phenyl]-(9CI);

N-[4-[1-hydroxy-2-[(1-methylethyl)amino]ethyl]phenyl]-methanesulfonamide, monohydrochloride;

(E)-1-[[[5-(4-chlorophenyl)-2-furanyl]methylene]amino]-3-[4-(4-methyl-1-piperazinyl)butyl]-2,4-imidazolidine-dione;

4-(2-isopropylamino-1hydroxyethyl)-methanesulfonanalide or a pharmaceutically acceptable salt thereof.

6. The method as recited in claim 4 wherein the class III antiarrhythmic compound is:

N-[4-[2-[methyl[2-4-[(methylsulfonyl)amino]phenoxy]ethyl]-phenyl]-methanesulfonamide;

N-(1-methylethyl)-N-[2-[(1-methylethyl)amino]ethyl]-4-(methylsulfonyl)-amino]-benzenesulfonamide;

a compound having the structure:

a compound having the structure:

a compound having the structure:

4-(3-(ethyl(3-(propylsulfinyl)propyl)-amino)-2-hydroxypropoxy)-benzonitrile;

methanesulfonanilide, N-[4-[[1-[2-(6-methyl-2-pyridinyl)ethyl]-4-piperidinyl]carbonyl]phenyl]-(9CI);

N-[4-[1-hydroxy-2-[(1-methylethyl)amino]ethyl]phenyl]
-methanesulfonamide, monohydrochloride;

(E)-1-[[[5-(4-chlorophenyl)-2-furanyl]methylene]amino]
-3-[4-(4-methyl-1-piperazinyl)butyl]-2,4-
imidazolidine-dione;

4-(2-isopropylamino-1hydroxyethyl)-
methanesulfonanalide or a pharmaceutically acceptable
salt thereof.

7. The method as recited in claim 1 wherein the potassium channel opener is administered in an amount from about 0.01 mg/kg to about 100 mg/kg.

8. The method as recited in claim 1 wherein the potassium channel opener is administered in an amount from about 1 mg/kg to about 10 mg/kg.

9. The method as recited in claim 1 where in the class III antiarrhythmic compound is administered in an amount from about 0.01 mg/kg to about 100 mg/kg.

10. The method as recited in claim 1 wherein the class III antiarrhythmic compound is administered in an amount from about 0.1 mg/kg to about 25 mg/kg.

11. The method as recited in claim 1 wherein said potassium channel opener in combination with said class III antiarrhythmic compound is administered orally or parenterally.

12. A pharmaceutical composition comprising a potassium channel opener having little or no effect on action potential duration in the heart, a class III antiarrhythmic compound and a pharmaceutically acceptable carrier.

13. The composition as recited in claim 12 wherein the potassium channel opener is a compound of formula 14. The composition as recited in claim 12 wherein the class III antiarrhythmic compound is:

N-[4-[2-[methyl[2-4-[(methylsulfonyl)amino]-phenoxy]ethyl]-phenyl]-methanesulfonamide;

N-(1-methylethyl)-N-[2-[(1-methylethyl)amino]ethyl]-4-[(methylsulfonyl)-amino]-benzenesulfonamide;

a compound having the structure:

a compound having the structure:

a compound having the structure:

4-(3-(ethyl(3-(propylsulfinyl)propyl)-amino)-2-hydroxypropoxy)-benzonitrile;
methanesulfonanilide, N-[4-[[1-[2-(6-methyl-2-pyridinyl)ethyl]-4-piperidinyl]carbonyl]phenyl]-(9CI);
N-[4-[1-hydroxy-2-[(1-methylethyl)amino]ethyl]phenyl]-methanesulfonamide, monohydrochloride;
(E)-1-[[[5-(4-chlorophenyl)-2-furanyl]methylene]amino]-3-[4-(4-methyl-1-piperazinyl)butyl]-2,4-imidazolidine-dione;

4-(2-isopropylamino-1hydroxyethyl)-methanesulfonanalide or a pharmaceutically acceptable salt thereof.

15. The composition as recited in claim 13 wherein the class III antiarrhythmic compound is:

N-[4-[2-[methyl[2-4-[(methylsulfonyl)amino]-phenoxy] ethyl]-phenyl]-methanesulfonamide;

N-(1-methylethyl)-N-[2-[(1-methylethyl)amino]ethyl]-4-(methylsulfonyl)-amino]-benzenesulfonamide;

a compound having the structure:

a compound having the structure:

a compound having the structure:

4-(3-(ethyl(3-(propylsulfinyl)propyl)-amino)-2-hydroxypropoxy)-benzonitrile;
methanesulfonanilide, N-[4-[[1-[2-(6-methyl-2-pyridinyl)ethyl]-4-piperidinyl]carbonyl]phenyl]-(9CI);
N-[4-[1-hydroxy-2-[(1-methylethyl)amino]ethyl]phenyl]-methanesulfonamide, monohydrochloride;
(E)-1-[[[5-(4-chlorophenyl)-2-furanyl]methylene]amino]-3-[4-(4-methyl-1-piperazinyl)butyl]-2,4-imidazolidine-dione;
4-(2-isopropylamino-1hydroxyethyl)-methanesulfonanalide or a pharmaceutically acceptable salt thereof.

* * * * *

UNITED STATES PATENT AND TRADEMARK OFFICE
CERTIFICATE OF CORRECTION

PATENT NO. : 5,679,706

DATED : Oct. 21, 1997

INVENTOR(S) : Albert J. D'Alonzo

It is certified that error appears in the above-identified patent and that said Letters Patent is hereby corrected as shown below:

In column 17, formula II, please replace structure with the following formula II structure:

Signed and Sealed this

Fourteenth Day of April, 1998

*Attest:*

*Attesting Officer*

BRUCE LEHMAN

*Commissioner of Patents and Trademarks*